(12) United States Patent  
Muecke et al.

(10) Patent No.: US 9,349,233 B2  
(45) Date of Patent: May 24, 2016

(54) PORTABLE MEDICATION DISPENSING CONTAINERS

(71) Applicant: CareFusion 303, Inc., San Diego, CA (US)

(72) Inventors: Melvin Muecke, Romona, CA (US); David Heffron, San Diego, CA (US); Peter Godlewski, San Clemente, CA (US)

(73) Assignee: CAREFUSION 303, INC., San Diego, CA (US)

( * ) Notice: Subject to any disclaimer, the term of this patent is extended or adjusted under 35 U.S.C. 154(b) by 8 days.

(21) Appl. No.: 14/298,274

(22) Filed: Jun. 6, 2014

(65) Prior Publication Data

US 2014/0285314 A1    Sep. 25, 2014

Related U.S. Application Data

(63) Continuation of application No. 13/354,172, filed on Jan. 19, 2012, now Pat. No. 8,749,379.

(51) Int. Cl.
| | |
|---|---|
| *G05B 19/00* | (2006.01) |
| *G05B 23/00* | (2006.01) |
| *G06F 7/00* | (2006.01) |
| *G06F 7/04* | (2006.01) |
| *G06K 19/00* | (2006.01) |
| *G07C 9/00* | (2006.01) |
| *E05G 1/10* | (2006.01) |
| *G08B 13/00* | (2006.01) |
| *A61J 7/00* | (2006.01) |

(Continued)

(52) U.S. Cl.
CPC ........... *G07C 9/00126* (2013.01); *A61J 7/0084* (2013.01); *E05G 1/10* (2013.01); *G06F 19/3462* (2013.01); *G07C 9/00896* (2013.01); *G08B 13/00* (2013.01); *A61J 1/1437* (2013.01); *G07C 2009/00761* (2013.01); *G07C 2009/00769* (2013.01); *G08B 13/1427* (2013.01)

(58) Field of Classification Search
CPC .................. G07C 9/00896; G07C 2009/00761; G07C 2009/00769; E05G 1/005; E05G 1/10
USPC ............. 340/5.3, 540, 541, 545.1, 5.21, 5.31, 340/5.7, 5.73; 109/45
See application file for complete search history.

(56) References Cited

U.S. PATENT DOCUMENTS

| | | |
|---|---|---|
| 5,615,625 A | 4/1997 | Cassidy et al. |
| 6,040,771 A | 3/2000 | Kim |

(Continued)

FOREIGN PATENT DOCUMENTS

WO        WO02076850        10/2002

OTHER PUBLICATIONS

International Search Report and Written Opinion for PCT/US2013/021778 mailed Apr. 19, 2013.

(Continued)

*Primary Examiner* — John A Tweel, Jr.  
(74) *Attorney, Agent, or Firm* — McDermott Will & Emery LLP

(57) ABSTRACT

A medication delivery system is disclosed that includes a portable container and a controller. The portable container includes a body and a lid that forms a securable storage compartment, and a latch that is coupled to the body and configured to releasably secure the lid. The portable container also includes a processor and a power source coupled to the latch, the processor causing the latch to release when an access signal based on a unique identifier is received.

17 Claims, 5 Drawing Sheets

(51) Int. Cl.
    *G06F 19/00*     (2011.01)
    *G08B 13/14*     (2006.01)
    *A61J 1/14*     (2006.01)

(56) References Cited

U.S. PATENT DOCUMENTS

| | | |
|---|---|---|
| 6,583,713 B1 | 6/2003 | Bates |
| 6,806,807 B2 | 10/2004 | Cayne et al. |
| 6,895,873 B1 | 5/2005 | Searle |
| 2003/0174554 A1 | 9/2003 | Dunstone et al. |
| 2008/0099367 A1 | 5/2008 | Niemiec et al. |
| 2011/0187530 A1 | 8/2011 | Sterzinger et al. |

OTHER PUBLICATIONS

Extended European Search Report for Application No. 13738992.0, dated Aug. 17, 2015, 5 pages.

PORTABLE MEDICATION DISPENSING CONTAINERS

CROSS-REFERENCE TO RELATED APPLICATIONS

The present application is a continuation of U.S. application Ser. No. 13/354,172, filed Jan. 19, 2012, now U.S. Pat. No. 8,749,379, which is incorporated herein by reference.

BACKGROUND

1. Field

The present disclosure is related to the use of secure portable containers to transport and dispense medications, particularly from a central automated dispensing machine (ADM) to the bedside of a patient.

2. Description of the Related Art

Patients in hospitals receive multiple medications on a regular schedule or on an as-needed basis, also known as "PRN" (meaning "when necessary" from the Latin "pro re nata"). Medications are frequently stored in an ADM that may be located at a nurse's station or other central location. Some ADMs, such as the Pyxis MedStation™, use secure transportable containers, such as the CUBIE® pockets used with the MedStation, to transfer medications between the filling location, for example a pharmacy, and the ADMs. Such a system is disclosed in U.S. Pat. No. 6,116,461 to Broadfield et al., for example. These containers are secure during transport and may be opened only after being placed in the ADM and after entry of the proper identification information by the nurse. Some hospitals utilize pharmacy systems that allow the pharmacists to enter approved prescriptions into the system. In these pharmacy systems, the ADMs are configured to require identification of the patient for which a medication is being requested, check whether that medication has been prescribed for that patient, and allow the nurse access to the medication only if the medication has been prescribed.

In some hospitals, the medication administration protocol requires nurses to travel to the ADM to dispense the medications for each individual patient at the time of administration. If a nurse is responsible for multiple patients, this can create numerous trips back and forth between the patients' rooms and the ADM. Nurses are subject to interruptions during these trips, further adding to the time that it takes to administer a medication to a patient.

SUMMARY

It is desirable to provide a system and method of securely storing medications while allowing nurses to carry the medications with them and dispense the medications at the bedside or other location away from the ADM, thereby avoiding the need for the nurses to return to the central ADM each time a medication is to be administered. It is further desirable to track the location of the securely stored medications and allow access to the securely stored medications only when the securely stored medications are in certain designated areas, and to provide an alarm if the securely stored medications are removed from an approved area. The portable containers and the dispensing systems disclosed herein provide at least this capability.

In certain embodiments, a portable container is disclosed that includes a body and a lid that cooperatively form a securable storage compartment and a latch that is coupled to the body and configured to releasably secure the lid. The portable container also includes a location-sensing element configured to determine a location of the portable container and provide the location, and a processor coupled to the latch and the location sensing element. The processor is configured to receive the location from the location-sensing element and allow the latch to release the lid upon a determination that the portable container is located in an area where access to the contents of the portable container is permitted.

In certain embodiments, a medication delivery system is disclosed that includes a plurality of portable containers each having a body with a lid forming a secure storage compartment and a latch that is coupled to the body and configured to releasably secure the lid. The system also includes a location-sensing element configured to determine a location of the portable container and provide the location, a memory comprising a unique identifier, and a first processor coupled to the latch, the location sensing element, and the memory. The first processor is configured to receive the location from the location sensing element, retrieve the identifier from the memory, provide an information signal comprising the location and identifier, receive an access signal, and cause the latch to release the lid upon receipt of the access signal. The system also includes a controller selectively coupled to the first processor of at least one of the portable containers. The controller includes a memory configured to store facility information related to at least one area of a facility and which of the plurality of portable containers are allowed to be opened within the at least one area, and a second processor configured to receive the information signal from the first processor, retrieve the facility information from the memory, compare the location of the at least one portable container to the facility information, and provide the access signal to the first processor if the at least one portable container is located in an area wherein the at least one portable container is allowed to be opened.

In certain embodiments, a portable container is disclosed that includes a body with a lid forming a securable storage compartment and a latch that is coupled to the body and configured to releasably secure the lid. The portable container also includes a processor coupled to the latch and a power source coupled to the latch and the processor. The processor is configured to receive an access signal from an external controller and cause the latch to release the lid upon receipt of the access signal.

In certain embodiments, a medication delivery system is disclosed that comprises a plurality of portable containers each having a body with a lid forming a securable storage compartment and a latch that is coupled to the body and configured to releasably secure the lid. The system also includes a first processor coupled to the latch, a power source coupled to the latch and the first processor, and a first memory coupled to the first processor. The first memory comprises a unique identifier. The first processor is configured to retrieve the unique identifier from the first memory, provide a data signal comprising the unique identifier, receive an access signal, and cause the latch to release the lid upon receipt of the access signal. The system also includes a controller that has a second processor communicatively coupled to the scanner and to the first processor of at least one of the portable containers. The second processor is configured to receive the data signal from the first processor of the at least one portable container, provide an information signal comprising a patient identifier and the portable container identifier to the server, and provide the access signal to the first processor upon a determination that the portable container is allowed to be opened. The system also includes a server configured to store information related to prescriptions for at least one patient, store information related to a content of at least one of the plurality of portable containers, and receive the information signal from the second processor.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The following description discloses embodiments of a system and method for providing secure portable storage of medications. Such a system allows authorized users to access the contents of the portable container. The disclosure describes the system and methods in the context of a medication dispensing system wherein medications are stored in the portable containers that are accessed by nurses for administration to patients in a healthcare setting.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Figure 1:
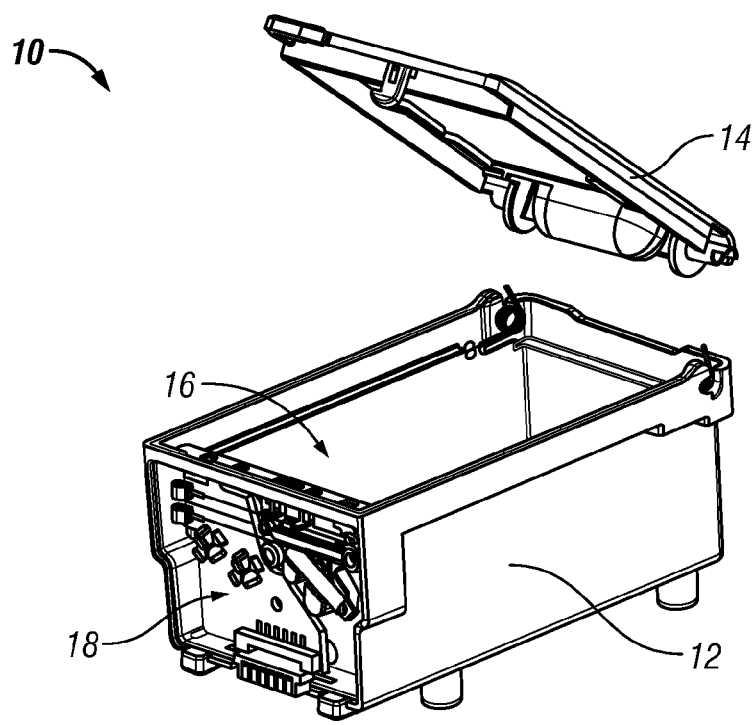
FIG. 1 is an exploded view of an exemplary portable container according to certain aspects of this disclosure.

FIG. 1 is an exploded view of an exemplary portable container 10 according to certain aspects of this disclosure. The portable container 10 comprises a body 12 and, in this embodiment, a lid 14 that is hingedly attached to the body 12. The body 12 and lid 14 together form a secure compartment 16. The portable container 10 includes electronics 18 that, in certain embodiments, provide communication and control capabilities. A cover has been removed from body 12 in FIG. 12 to reveal the enclosed electronics 18. In certain embodiments, the lid 14 is releasably securely by a powered latch (not visible in FIG. 1) that is activated by an internal processor (not visible in FIG. 1) that are both part of the electronics 18. The internal elements of the portable container 10 are discussed in greater detail with respect to FIG. 3. In certain embodiments, the lid 14 is clear to allow inspection of the contents of the portable container 10 without releasing the lid 14.

Figure 2:
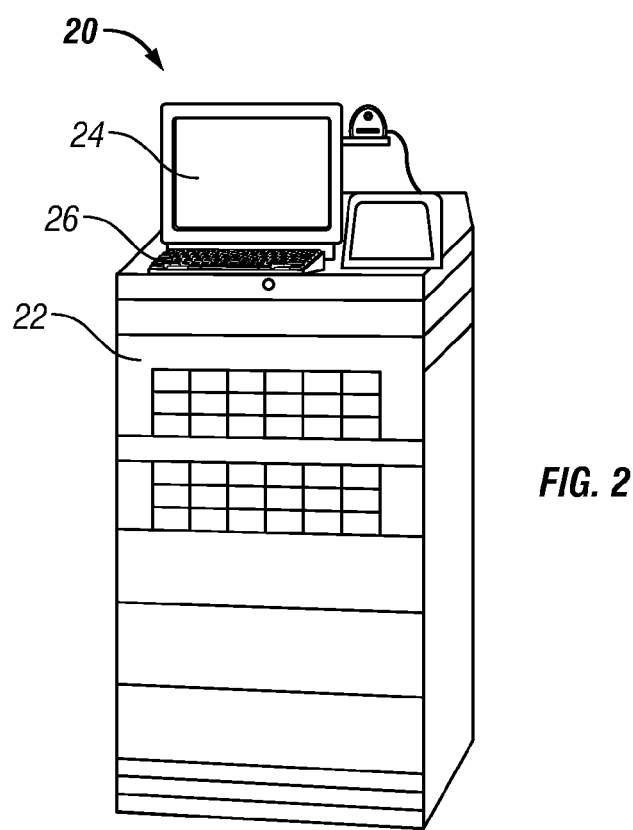
FIG. 2 depicts an exemplary ADM configured to utilize secure portable containers according to certain aspects of this disclosure.

FIG. 2 depicts an exemplary ADM 20 configured to utilize secure portable containers 10 according to certain aspects of this disclosure. In certain embodiments, the portable containers 10 are stored in drawers 22. In certain embodiments, the drawers 22 comprise a plurality of power connectors (not visible in FIG. 2) configured to provide power and signals to portable containers 10. In certain embodiments, a nurse or other user can provide information through a touch screen 24, keyboard 26, or other input device such that the ADM 20 allows the nurse to remove one or more of the portable containers 10 from the drawer 22.

Figure 3:
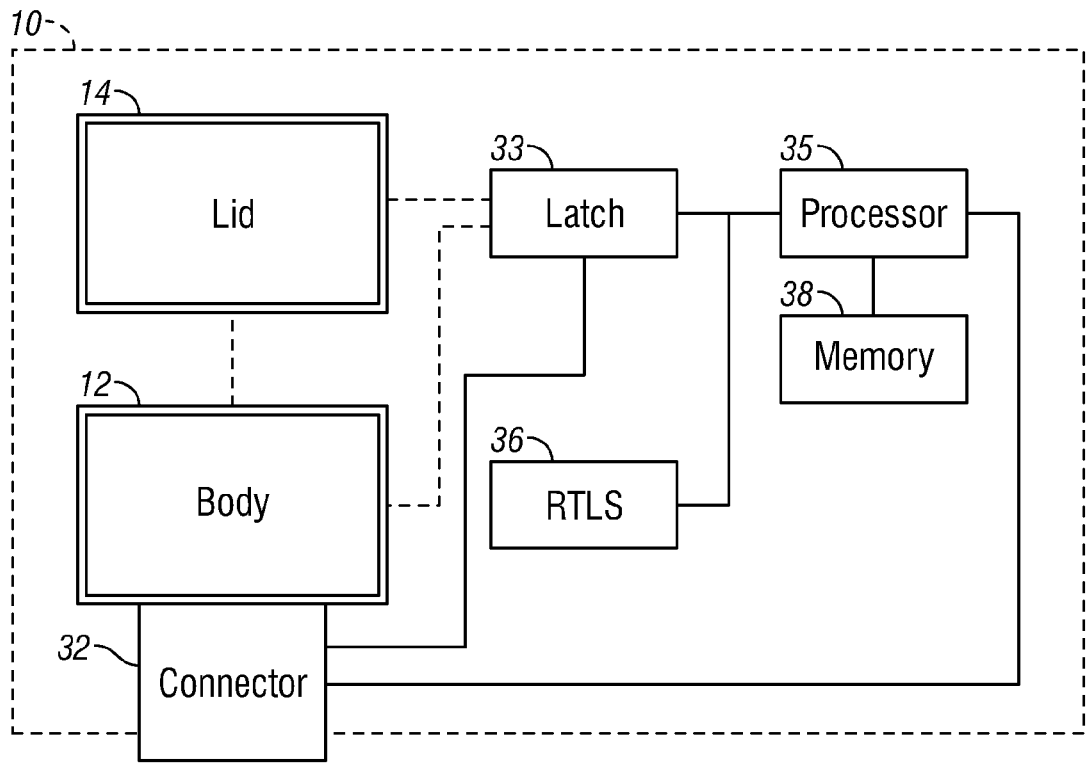
FIG. 3 is a block diagram of one embodiment of the portable container of FIG. 1 according to certain aspects of this disclosure.

FIG. 3 is a block diagram of one embodiment of a portable container 10 of FIG. 1 according to certain aspects of this disclosure. In addition to the body 12 and lid 14 described with respect to FIG. 1, the portable container 10 comprises a latch 33 that is coupled to the body 12 and configured to releasably secure the lid 14 such that the contents of the secure compartment 16 are not accessible when the lid 14 is secured and are accessible when the lid 14 is released by the latch 33. The latch 33 is coupled to a processor 35 that is configured to selectably cause the latch 33 to release the lid 14. In certain embodiments, the portable container 10 comprises a connector 32 that is coupled to the body 10 and the latch 33, the function of the connector 32 being described in greater detail with respect to FIG. 4. In certain embodiments, the portable container 10 comprises a memory 38 coupled to the processor 35. In certain embodiments, the memory comprises a unique identifier associated with the portable container 10.

In certain embodiments, the portable container 10 comprises a real time locating system (RTLS) element 36 that is configured to determine the location of the portable container 10 within a facility. In certain embodiments, the facility has a wireless system that communicates with the RTLS element 36 and provides reference information that allows the RTLS element 36 to determine its location. In certain embodiments, the RTLS element 36 provides an identifier to the facility's wireless system and the system determines the location of the RTLS element 36. In certain embodiments, the facility's wireless system provides this location information to the RTLS element 36.

Figure 4:
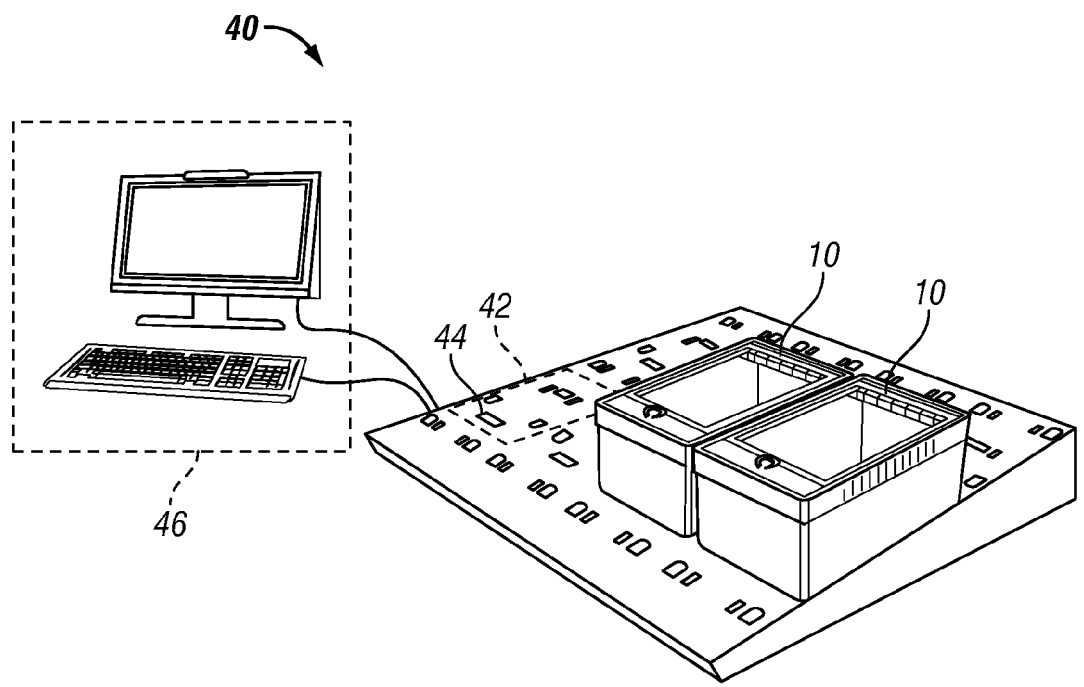
FIG. 4 is an exemplary dispensing station according to certain aspects of this disclosure.

FIG. 4 is an exemplary dispensing station 40 according to certain aspects of this disclosure. The dispensing station 40 comprises at least one docking station 42 configured to accept portable containers 10 and in the embodiment of FIG. 4, a plurality of docking stations 42. In certain embodiments, the docking station 42 comprises a docking connector 44 configured to mate with the connector 32 of the portable container 10. In certain embodiments, the docking connector 44 provides power to the latch 33 such that the lid can only be released when the portable container 10 is docked to the dispensing station 40. In certain embodiments, the dispensing station 40 comprises a user interface 46 that provides the same access control capability as provided by the ADM of FIG. 2, thereby allowing the nurse to access the secure compartments 16 of portable containers 10 that are docked to the dispensing station 40.

Figure 5:
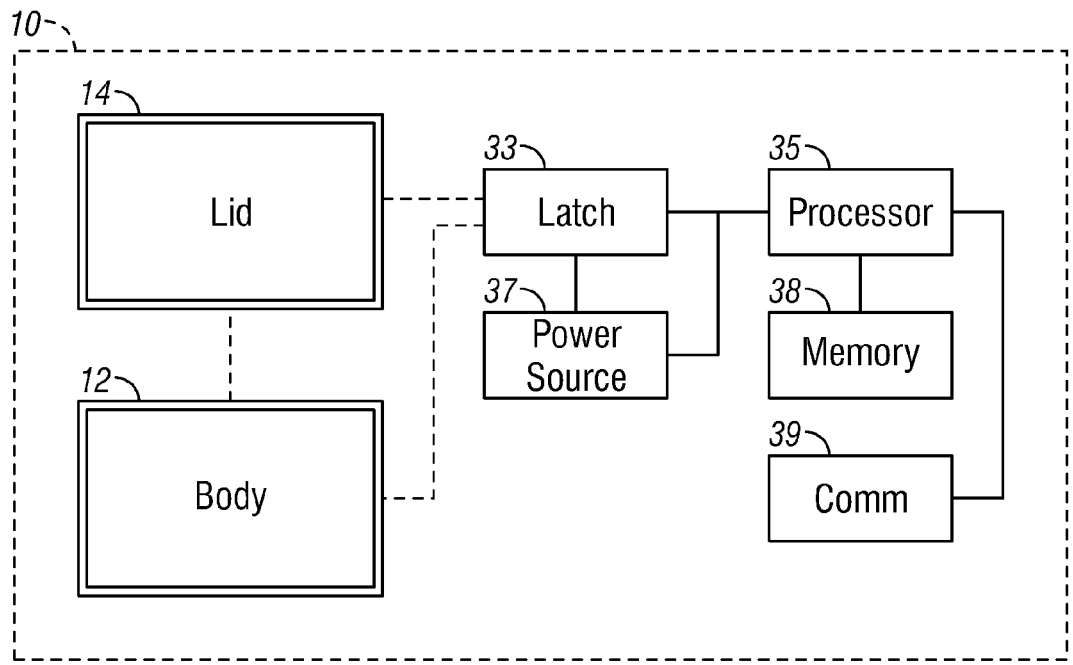
FIG. 5 is a block diagram of another embodiment of the portable container of FIG. 1 according to certain aspects of this disclosure.

FIG. 5 is a block diagram of another embodiment of the portable container 10 of FIG. 1 according to certain aspects of this disclosure. In certain embodiments, the lid 14, body 12, and latch 33 are configured in a manner similar to that of FIG. 3, with the latch 33 configured to releasably secure the lid 14 to the body 12 so as to form a secure storage compartment 16. The latch 33 is controlled by processor 35. In certain embodiments, a power source 37, for example a battery, is coupled to both the processor 35 and the latch 33 such that the portable container 10 is a self-contained functional unit that does not need to be docked to a power source, such as in FIG. 4, to release the lid 14. In certain embodiments, the portable container 10 comprises a communication device 39 configured to communicate with a hospital system, for example an Ethernet network. In certain embodiments, the communication device 39 is a radio frequency (RF) unit. In certain embodiments, the communication device 39 utilizes optical radiation to communicate with the hospital system. In certain embodiments, the communication device 39 utilizes infrared light to communicate with the hospital system. In certain embodiments, the portable container 10 comprises a memory 38 that comprises a unique identifier associated with this specific portable container 10.

Figure 6:
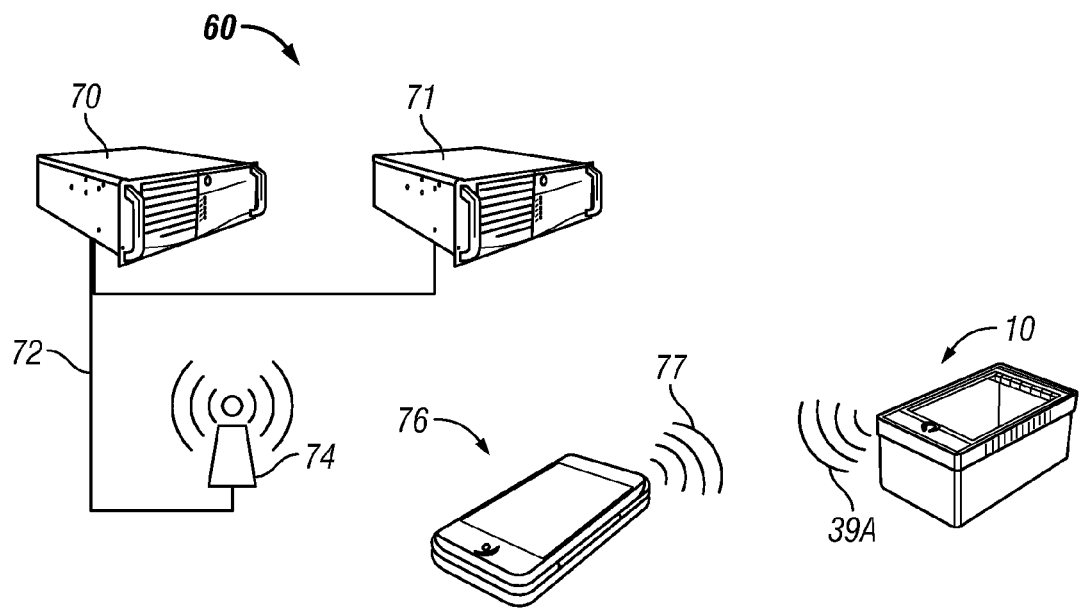
FIG. 6 is another embodiment of a medication dispensing system according to certain aspects of this disclosure.

FIG. 6 is another embodiment of a medication dispensing system 60 according to certain aspects of this disclosure. In certain embodiments, the medication dispensing system 60 comprises a portable container 10 communicatively coupled to a controller 76 through, in this embodiment, wireless signals 39A and 77. In certain embodiments, the wireless signals 39A and 77 are RF signals. In certain embodiments, the wireless signals 39A and 77 are optical signals. In certain embodiments, the controller 76 and portable container 10 respectively comprise connectors (not visible in FIG. 6) configured to mate and establish a direct communication link between the controller's processor (not shown in FIG. 6) and the portable container's processor 35 (not shown in FIG. 6). The controller 76 is also communicatively coupled to a wireless access point 74 that is further coupled to a communication network 72, such as a wired Ethernet network. The system 60 also comprises one or more servers 70, 71 that are communicatively coupled to the network 72 and, therefore, communicatively coupled to the controller 76. In certain embodiments, server 70 is a pharmacy server comprising prescriptions for patients. In certain embodiments, server 71 is a RTLS server comprising information about the layout of the hospital. In certain embodiments, the RTLS server 71 comprises a controller (not visible in FIG. 6) that interacts with at least the processor 35 and RTLS element 36 of the portable container 10 embodied in FIG. 3 to determine the location of the portable container 10 and provide an access signal to the processor 35 if the portable container is located in an area where access to the contents of the portable container 10 is permitted.

Figure 7:
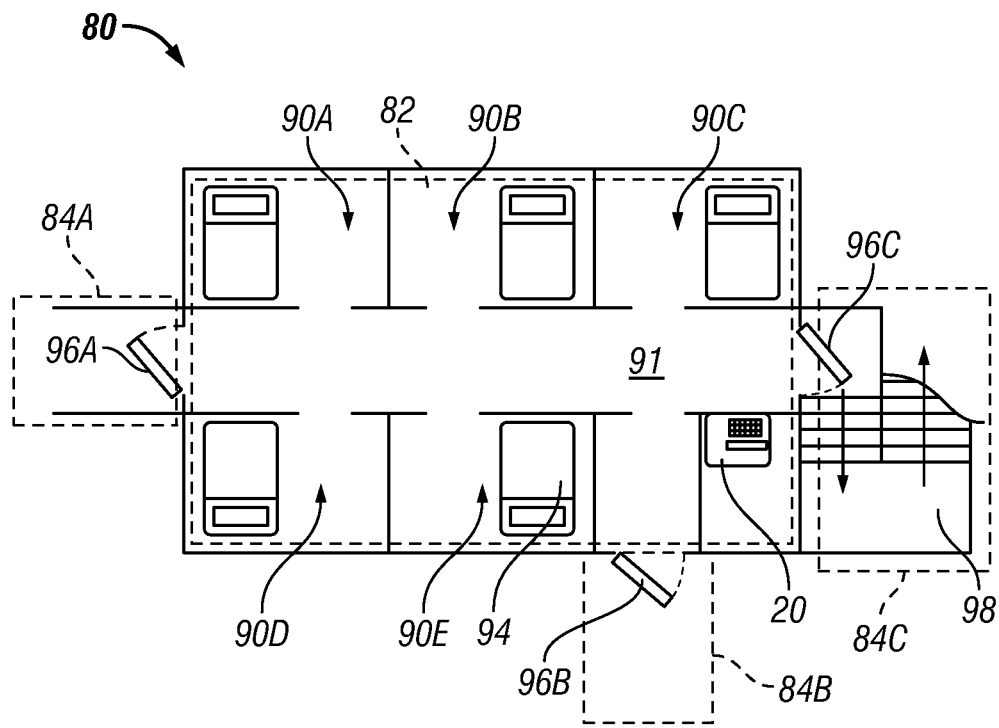
FIG. 7 is a simplified schematic of a hospital with defined zones according to certain aspects of this disclosure.

FIG. 7 is a simplified schematic 80 of a hospital with defined zones 84 according to certain aspects of this disclosure. In this example, a care unit has five patient rooms 90A-90E and an ADM 20. There are three doors 96A, 96B, and 96C that lead out of the care unit, with door 96C leading into stairwell 98. A zone 82 has been defined to include care unit rooms 90A-90E and hallway 91. Zones 84A, 84B, i.e. other parts of the hospital, have been defined outside of doors 96A, 96B, respectively, and zone 84C has been defined outside of door 96C which leads to the outside of the hospital. The server 70 of FIG. 6 may include a database that defines which zones are approved for each of the portable containers 10 that are being used by the hospital. The server 70 may be configured to provide an alert if the portable container 10 is determined to be in a zone that is not approved for that portable container 10. For example, a portable container 10 may be allowed in zone 82 as well as zones 84A, 84B but not allowed in zone 84C. In this manner, removal of the portable container 10 from the hospital will create an alert when the portable container 10 is detected in zone 84C.

Figure 8:
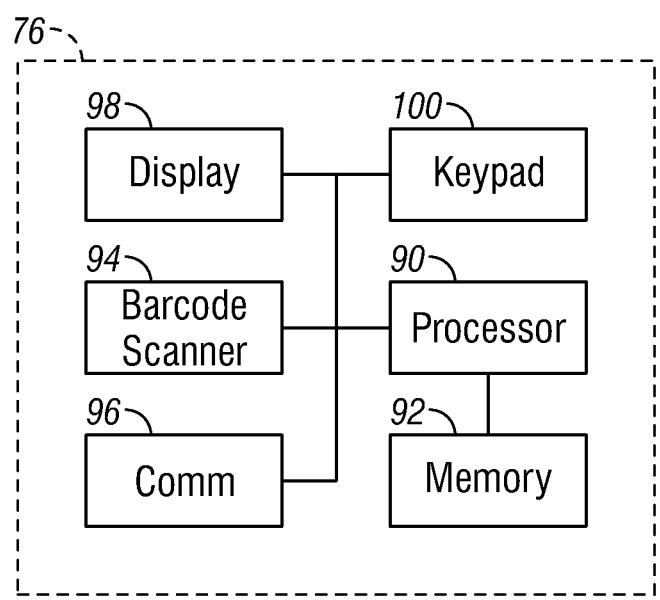
FIG. 8 is an exemplary block diagram of a handheld controller according to certain aspects of this disclosure.

FIG. 8 is an exemplary block diagram of a handheld controller 76 according to certain aspects of this disclosure. The controller 76 comprises a processor 90 coupled to a memory 92 configured to store at least programs and data. The processor 90 is also coupled to a communication element 96, a display 98 and a keypad 100. In certain embodiments, the communication element 96 comprises a wireless network communication capability, such as an 802.11 transceiver. In certain embodiments, the communication element 96 comprises a local wireless communication capability, such as a Bluetooth® or infrared transceiver. In certain embodiments, the keypad 100 is replaced by other input devices such as a touchpad overlaying the display 98. The processor 90 is also coupled, in this embodiment, to scanner 94, shown in FIG. 8 as an exemplary barcode scanner 94. In certain embodiments, the barcode scanner 94 is replaced by a radio frequency identification (RFID) scanner. In certain embodiments, the barcode scanner 94 is replaced by a device capable of scanning and interpreting machine-readable elements containing information and providing such information to the processor 90. The configuration of FIG. 7 is exemplary and not limiting, as a variety of standard and custom handheld controllers may be employed to provide the capabilities described in this disclosure.

Figure 9:
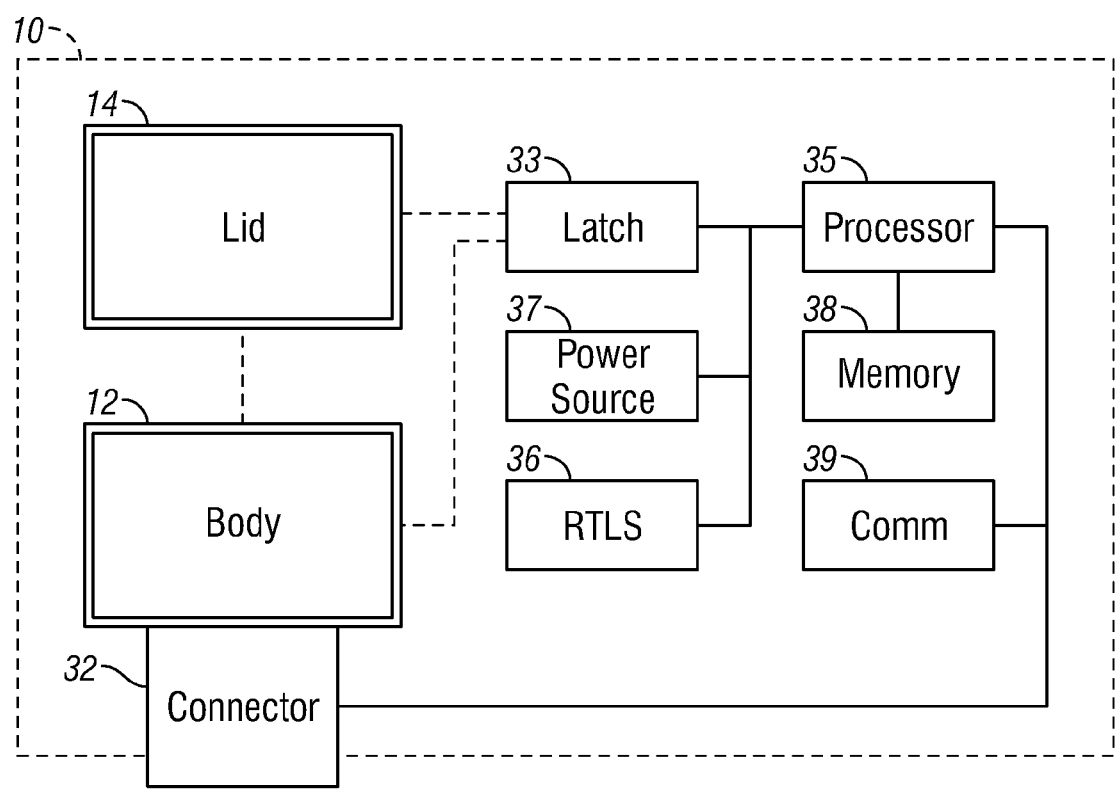
FIG. 9 is a block diagram of another embodiment of the portable container of FIG. 1 according to certain aspects of this disclosure.

FIG. 9 is a block diagram of another embodiment of the portable container 10 of FIG. 1 according to certain aspects of this disclosure. In this embodiment, the portable container comprises a processor 35 coupled to a memory 38 and a latch 33 that releasably secures the lid 14 to the body 12. The embodiment of FIG. 9 also includes a RTLS element 36, a connector 32, and a communication device 39 as well as a power source 37, thereby combining the features of the embodiments of FIGS. 3 and 5.

The following discussion provides non-limiting examples of how portable container 10 may be used in a hospital. Other methods of utilizing portable container 10, and combinations of the features of the embodiments of the portable container 10 described in FIGS. 3 and 5, will be obvious to those of skill in the art.

In a first example, an exemplary use of a RTLS-enabled portable container 10, such as shown in FIGS. 1-4 is disclosed. A nurse enters her identification information into the ADM 20 of FIG. 2, located in a care unit as shown in FIG. 7, and then enters the identification of a patient. The ADM 20 is configured to display the prescribed medications for this patient, and the nurse reviews the displayed prescriptions to determine what medications are to be administered to the patient. In this example, the nurse identifies to the ADM 20 a medication that she wishes to remove from the ADM 20, and the ADM 20 opens the appropriate drawer 22 and releases the portable container 10 that contains the identified medication. The nurse removes the portable container 10, closes the drawer 22, and logs out of the ADM 20.

As the nurse moves about the care unit 82 with the portable container 10, the RTLS element 36 tracks the location of the portable container 10. In this example, the hospital wireless system includes a RTLS server 71, such as server 71 of FIG. 6, that receives periodic messages from the RTLS element 36 and tracks the portable container 10 by triangulation of each message through the access points 74 that are part of the hospital network system. In other embodiments, a standalone RTLS system may be used. In certain embodiments, a RTLS system may utilize any of the real time locating methods of determining the location of the RTLS element 36 as known to those of skill in the art. The RTLS server 71 includes a layout of the hospital, such as shown in FIG. 7, and is configured to determine where the portable container 10 is located with respect to this layout 80. The layout 80 includes one or more defined areas. In this example, the area 82 is defined to be the care unit in which the ADM 20 and the patient are located and areas 84A, 84B, and 84C are defined to include the rest of the hospital. Furthermore, the RTLS server 71 includes a database that defines what areas are approved for each portable container 10. In this example, the portable container 10 is approved for area 82 and not approved for areas 84A, 84B, or 84C. As long as the portable container 10 remains within area 82, the RTLS server 71 takes no action. If the RTLS server 71 determines that the portable container 10 is located in any of areas 84A, 84B, and 84C, the RTLS server 71 issues an alert. In certain embodiments, the alert is provided via a pager to the nurse or other nursing staff. In certain embodiments, the alert is provided to other staff such as a receptionist or security staff.

When the nurse arrives at the bedside of the patient, for example in room 90D, for whom the medication contained in the portable container 10 is prescribed, the nurse places the portable container 10 in a docking station 42 of a dispensing station 40 (not visible in FIG. 7) that is located in the patient's room 90D. The nurse uses the user interface 46 (not visible in FIG. 7) to request access to the contents of the portable container 10. The processor 35 communicates with the RTLS element 36 which returns a signal that the portable container 10 is located in an approved area, and the processor 35 causes the latch 33 to release the lid 14, providing access to the medication. In certain embodiments, the processor 35 communicates with the server 71 to determine whether the portable container 10 is located in an approved area.

In a second example, an exemplary use of a battery-powered portable container 10 is disclosed. A nurse interacts with the ADM 20 in the same manner as described in the previous example and removes a portable container 10 having a power source 37 and a communication device 39. When the nurse arrives at the bedside of the patient in room 90D, the nurse logs in to her handheld controller 76 and activates a program for accessing the portable container 10. The controller 76, in this example, requests that the nurse identify herself and she scans a barcode on her identification badge using a built-in scanner of the controller 76. The controller 72 then requests that the patient be identified, and the nurse scans a barcode printed on a wristband worn by the patient, wherein the barcode comprises the patient's identification code. The controller 76 sends this information to a pharmacy server, such as server 70 of FIG. 6, that comprises databases that comprise prescriptions for patients in the hospital and the contents of portable containers 10 in the hospital. The pharmacy server 70 verifies that the medication contained in the portable container 10 in which the processor 35 is located is prescribed for the identified patient and provides an access approval signal to the controller 76. Upon receipt of the access signal from the server 70, the controller 76 sends an access signal through the communication device 39 to the processor 35 of the portable container 10. The processor 35 then causes the latch 33 to release the lid 14 drawing power from the power source 37, thereby providing access to the contents of the portable container 10. Hence, with the embodiment of FIGS. 5 and 6, a docking station 40 is not required to open a portable container 10.

In certain embodiments, the communication device 39 of FIG. 5 is connected to an external connector and the controller 76 has a matching connector (not shown in FIG. 6) such that the portable container 10 is plugged into the controller 76 to exchange signals instead of communicating wirelessly.

In certain embodiments, the portable container 10 has been assigned to a patient and the identification of the assigned patient is stored in the memory 38. The controller 76 retrieves the stored patient identification using processor 35 and compares it to the scanned patient identification to determine whether the portable container 10 is assigned to the scanned patient. If so, the controller 76 sends the access signal through the communication device 39 to the processor 35 of the portable container 10.

Portable containers 10 may have any or all of the features and elements shown in the block diagrams of FIGS. 3 and 5. A portable container 10 having a wireless communication capability, for example through communication device 39 configured to communicate with a wireless Ethernet system, a RTLS capability, for example through a RTLS element 36, and a power source 37, such as a battery, can provide a variety of capabilities for secure portable storage while allowing access to the stored items, for example medications. The RTLS capability can prevent theft or loss by triggering an alert if the portable container 10 is taken outside of an approved area, for example off a specific floor of the hospital, as well as allowing a lost portable container 10 to be found through the RTLS server 71. The communication capability, which may be provided in any of a variety of wired or wireless forms, allows any portable device, such as a cell phone or portable digital assistant (PDA), having a matching communication capability to control the portable container 10 in the same manner as accomplished by the ADM 20.

The disclosed systems and methods provide a portable container that includes a secure storage compartment. The portable container can be carried by the caregiver and accessed at the bedside or other location that is away from the central ADM. In certain embodiments, the portable container is battery powered and the caregiver can use a handheld controller, such as a cell phone, to provide the access signals to cause the latch to release the lid thereby providing access to the contents of the secure storage compartment of the portable container. In certain embodiments, the portable container comprises a RTLS device that periodically provides the location of the portable container to an external system.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims.

Reference to an element in the singular is not intended to mean "one and only one" unless specifically so stated, but rather "one or more." Unless specifically stated otherwise, the term "some" refers to one or more.

The term "optical" as used herein refers to electromagnetic radiation from ultraviolet to infrared, including wavelengths in the range of 10 nanometers to 1 millimeter and includes, but is not limited to, light visible to the human eye, which covers the range of 380-760 nanometers.

The phrase "Radio Frequency Identification" and the acronym "RFID" include systems wherein a scanner having an antenna communicates wirelesly with multiple devices, or tags, that are equipped with antennas for the purpose of retrieving one or more items of information related to the tag or an item to which the tag is attached. This communication may occur at any frequency with the band of 3 kHz to 300 GHz. The tag may be passive, i.e. drawing power from the electromagnetic field created the scanner antenna, or active, having a power source which may be internal, such as a battery, or external, such as a power coupling to a second device.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "operation for."

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A medication delivery system comprising:
   at least one portable container comprising:
   a body with a lid forming a securable storage compartment;
   a latch coupled to the body, the latch configured to releasably secure the lid;
   a first processor coupled to the latch;
   a first memory coupled to the first processor, the first memory comprising a unique identifier; and
   a power source coupled to the latch and the first processor;
   wherein the first processor is configured to:
   retrieve the unique identifier from a first memory;
   provide a data signal comprising the unique identifier;
   receive an access signal; and
   cause the latch to release the lid upon receipt of the access signal;
   a connector coupled to the body and the latch, wherein the body is configured to mate with a docking station having a docking connector, wherein the connector of the portable container is configured to mate with the docking connector, receive power from the docking connector, and provide the power to the first processor and the latch; and
   a controller comprising a second processor communicatively coupled to a scanner and to the first processor of the at least one portable container, the second processor configured to:
   receive the data signal from the first processor of the at least one portable container; and
   provide the access signal to the first processor upon a determination that the portable container is allowed to be opened.

2. The medication delivery system of claim 1, wherein the second processor is further configured to provide an information signal comprising a patient identifier and the portable container identifier, and the medication delivery system further comprises a server configured to:
   store information related to prescriptions for at least one patient;
   store information related to a content of the at least one portable container; and
   receive the information signal from the second processor.

3. The medication delivery system of claim 2, wherein:
   the at least one portable container contains a medication;
   the prescription information stored on the server comprises a listing of medications to be administered to the at least one patient;
   the content information stored on the server comprises a list of at least one medication stored in the at least one portable container;
   the server is further configured to provide the prescription information for the identified patient and the container content information for the identified portable container upon receipt of the information signal; and
   the second processor is further configured to:
   receive the prescription information and the container content information from the server; and
   determine whether the at least one portable container is allowed to be opened.

4. The medication delivery system of claim 2, wherein:
   the at least one portable container contains a medication;
   the prescription information stored on the server comprises a listing of medications to be administered to the at least one patient;
   the content information stored on the server comprises a list of at least one medication stored in the at least one portable container; and
   the server is further configured to:
   retrieve prescription information for the identified patient;
   retrieve the content information for the identified portable container;
   compare the medications listed in the retrieved prescription information to the list of medications in the retrieved content information; and
   provide a permission signal to the second processor if at least one of the medications listed in the content information matches at least one of the medications listed in the prescription information; and
   the second processor is further configured to:
   receive the permission signal from the server; and
   provide the access signal upon receipt of the permission signal.

5. The medication delivery system of claim 1, wherein:
   the controller further comprises a scanner configured to:
   retrieve a patient identity from a machine-readable element associated with a patient, and provide the patient identity to the second processor; and the second processor is further configured to receive the patient identity from the scanner.

6. The medication delivery system of claim 1, wherein the portable container further comprises a location-sensing element configured to determine a location of the portable container.

7. The medication delivery system of claim 6, wherein the first processor is coupled to the location-sensing element and the first processor is configured to allow the latch to release the lid upon a determination that the portable container is located in an area where access to contents of the portable container is permitted.

8. The medication delivery system of claim 1, wherein the lid is configured to be released only when the portable container is docked to the docking station.

9. The medication delivery system of claim 1, wherein the controller is an external controller and the first processor is configured to provide the location received from the location-sensing element to the external controller.

10. The medication delivery system of claim 9, wherein the first processor is further configured to:
accept an access request from a user; and
provide the location information to the external controller upon receipt of the access request.

11. The medication delivery system of claim 1, wherein the portable container further comprises a battery coupled to the first processor and the latch.

12. A method of storing and dispensing medications, the method comprising the steps of:
placing at least one medication in a portable container that comprises a power source and a latch configured to releasably secure a lid that cooperates with a body to form a secure storage compartment;
determining automatically whether it is permissible to dispense the at least one medication, comprising the steps of:
determining with a scanner the identity of a patient;
retrieving from a coupled memory a list of medications that are prescribed for the identified patient;
retrieving from a memory of the portable container a unique identifier;
retrieving from a coupled memory a list of the at least one medication stored in the identified portable container; and
determining that it is permissible to dispense the at least one medication if at least one of the at least one medication stored in the identified portable container is prescribed for the identified patient; and
releasing the lid of the portable container automatically when it is determined that it is permissible to dispense the at least one medication.

13. The method of claim 12, further comprising the step of:
transporting the secured portable container to a location proximate to a patient, wherein the location proximate to the patient is within an area where it is allowable to dispense the at least one medication.

14. The method of claim 12, further comprising the steps of:
determining the location of the portable container; and
issuing an alert if the portable container is determined to be in an area into which the portable container is not allowed to be taken.

15. A non-transitory computer-readable medium having computer-executable instructions stored thereon for execution by a processor to perform a method of storing and dispensing medications, the method comprising the steps of:
determining automatically whether it is permissible to dispense at least one medication that is contained in a secure storage compartment of a portable container that comprises a power source and a latch configured to releasably secure a lid that cooperates with a body to form the secure storage compartment, comprising the steps of:
determining with a scanner the identity of a patient;
retrieving from a coupled memory a list of medications that are prescribed for the identified patient;
retrieving from a memory of the portable container a unique identifier;
retrieving from a coupled memory a list of the at least one medication stored in the identified portable container; and
determining that it is permissible to dispense the at least one medication if at least one of the at least one medication stored in the identified portable container is prescribed for the identified patient; and
releasing the lid of the portable container automatically when it is determined that it is permissible to dispense the at least one medication.

16. The non-transitory computer-readable medium of claim 15, further comprising the step of transporting the secured portable container to a location proximate to a patient, wherein the location proximate to the patient is within an area where it is allowable to dispense the at least one medication.

17. The non-transitory computer-readable medium of claim 15, further comprising the steps of:
determining the location of the portable container; and
issuing an alert if the portable container is determined to be in an area into which the portable container is not allowed to be taken.

* * * * *